United States Patent [19]

Joo

[11] Patent Number: 5,729,346
[45] Date of Patent: Mar. 17, 1998

[54] METHOD AND APPARATUS FOR TESTING AUTOMATIC INSERTION STATE OF ELECTRONIC COMPONENT IN PRINTED CIRCUIT BOARD

[75] Inventor: Iel-Kwen Joo, Seoul, Rep. of Korea

[73] Assignee: Daewoo Electronics Co., Ltd., Seoul, Rep. of Korea

[21] Appl. No.: 715,240

[22] Filed: Sep. 18, 1996

[30] Foreign Application Priority Data

Sep. 19, 1995 [KR] Rep. of Korea .................. 95-30820

[51] Int. Cl.$^6$ .................................................. G01B 11/00
[52] U.S. Cl. ........................ 356/394; 356/388; 356/400
[58] Field of Search ................................. 356/394, 401, 356/400, 388, 392

[56] References Cited

U.S. PATENT DOCUMENTS

| 5,329,359 | 7/1994 | Tachikawa | 356/398 |
| 5,408,189 | 4/1995 | Swart et al. | 356/401 |

Primary Examiner—Frank G. Font
Assistant Examiner—Reginald A. Ratliff
Attorney, Agent, or Firm—Beveridge, DeGrandi, Weilacher & Young LLP

[57] ABSTRACT

Disclosed is a method and an apparatus capable of easily and quickly testing an automatic inserting state of an electronic component in a printed circuit board using a slit light. The method and the apparatus makes use of a slit light type instead of using the conventional testing jig in order to test an automatic insertion state of an electronic component in a printed circuit board. Thus, the problem of a noise generated when applying a signal which indicates that the contacting pins of the electronic component contacting with pins of a jig are testing incorrect, can be solved. Also, the setup time of an apparatus for testing an automatic insertion state of an electronic component in a printed circuit board according to changing a design of the printed circuit board can be reduced.

15 Claims, 10 Drawing Sheets

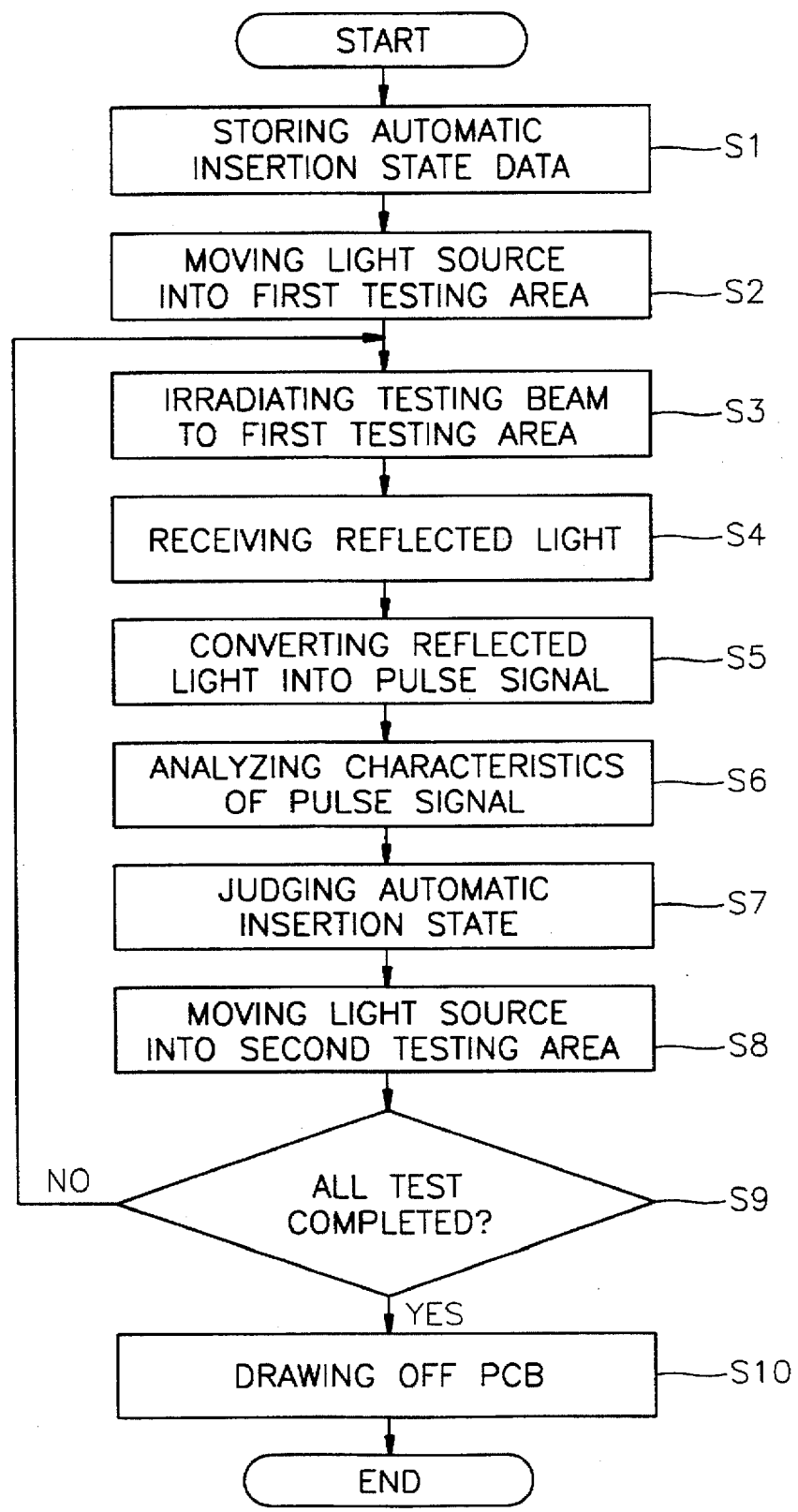

METHOD AND APPARATUS FOR TESTING AUTOMATIC INSERTION STATE OF ELECTRONIC COMPONENT IN PRINTED CIRCUIT BOARD

BACKGROUND OF THE INVENTION

1. Field of the Invention

The present invention relates to a printed circuit board (hereinafter referred to as "PCB"). More particularly, the present invention relates to a method and an apparatus capable of easily and quickly testing an automatic inserting state of an electronic component in a PCB using a slit light.

2. Description of the Prior Art

An internal is used for codecting a number of parts in order to attain an operation of a device which performs the operation. A PCB is comprised of several electronic components that are integrated on a small panel. The greatest distribution of the electronic components is manufactured by a printing method. Currently, printed circuit boards of a single pattern contain a high density of electronic components in order to reduce the size of both faces of the board. Because electronic machines tend to be popular, printed circuit boards with a single pattern have been manufactured in large quantities at one time.

Hereinafter, a configuration and the operation of the conventional apparatus 10 for testing an automatic inserting state of an electronic component in a printed circuit board will be described with reference to the accompanied drawings. FIG. 1 shows a configuration of a conventional apparatus 10 for testing an automatic inserting state of an electronic component in a printed circuit board. In an operation of the conventional apparatus 10 for testing an automatic inserting state of an electronic component in a printed circuit board, a jig 13 including a plurality of pins 14 arranged thereon is closely adhered to the bottom of PCB 11 having a plurality of electronic components 12 therein by an operation of a cylinder (not shown). Therefore, pins 14 are contacted with pins 121 and 122 of an electronic component 12. Then, a signal processing section 16 detects the automatic insertion state of electronic component 12 for such states as an incorrect insertion, a reverse insertion, a non-insertion, a short state, and a normal state by applying a suitable electric signal to pins 14 of jig 13 through a relay controlling section 15.

As mentioned previously, the conventional apparatus 10 for testing an automatic insertion state of an element in a printed circuit board has disadvantages as follows. (1) In order to adhere jig 13 to PCB 11, a cylinder (not shown) should be operated. Thus, jig 13 is vibrated and it generates a noise. (2) Because signal processing section 16 applies a predetermined electric signal to electronic component 12 through pin 14 of jig 13 and pin 121 of electronic component 12, the predetermined electric signal to element 12 becomes incorrect due to a pin 14 of jig 13 and pins 121 and 122 of electronic component 12 being in a connected state. (3) When jig 13 is contacted with electronic component 12, electronic component 12 which is inserted into PCB 11 due to a pressure happens to get damaged. (4) When changing a design of PCB 11, a replacing and repairing operation for resetting a position of pin 14 of jig 3 is needed. (5) Since jig 13 is frequently used, pin 14 of jig 13 is bent. Thus, it causes mistakes the operation.

U.S. Pat. No. 5,329,359, (issued to Jan. Tachikawa on Jul. 12, 1994) discloses one example of a method and an apparatus for testing an automatic inserting state of an electronic component in a printed circuit board. An object of U.S. Pat. No. 5,329,359 to provide a parts mounting inspection method capable of setting a small distance between parts and the inspection device without construction in terms of mounting intervals of the parts and heights and also causing errors in measurement values even when a density difference exists.

The parts mounting inspection method according to U.S. Pat. No. 5,329,359 includes the steps of providing a moving device for moving a stage holding a circuit board, a light source for irradiating the parts with a laser beam, an optical system path for irradiating the parts with the laser beam from the light source, a signal output path for outputting a reference signal by the laser beam from the light source, and a processing section for processing a signal from each other of the optical system path and the signal output path; obtaining reference signals A and B at first and second position, respectively, of the parts; holding the parts in the first position and irradiating the optical system path and the signal output path with the laser beam to detect a signal from each path, and outputting from the processing section a first phase difference signal, corresponding to the first position, of output from each path; moving the parts to the second position by the moving device; holding the parts in the second position and irradiating the optical system path and the signal output path with the laser beam to detect a signal from each path, and outputting from the processing section a second phase difference signal, corresponding to the second position, of output from each path; and determining the posture of the parts by comparison of the reference signals A and B, and the first phase difference signal in the first position and the second phase difference signal in the second position, the determination being made using a comparison signal which is a phase difference of the reference signals A and B in the first and second positions and a difference signals in the first and second positions.

U.S. Pat. No. 5,408,189, (issued to Mark A. Swan, Charles J. Johnson and David R. Van Loan on Apr. 18, 1995) discloses another example of a method and an apparatus for testing an automatic inserting state of an electronic component in a printed circuit board. An object of U.S. Pat. No. 5,408,189 to provide test fixture alignment system for PCB capable of accurately positioning a printed circuit board on a test fixture so that a pattern of test points in a circuit array printed on the board is precisely registered with an array of corresponding test probes on the fixture.

The test fixture alignment system for PCB according to U.S. Pat. No. 5,408,189 includes a tooling pin rigidly affixed to a board mounting plate for engaging the alignment device on a PCB and its circuit array in a fixed position relative to the array of test probes on the probe plate; a sensor mounted in a fixed position for sensing the position of the fiducial mark as the board moves relative to the sensor and the array of test probes to produce an output representative of the alignment or misalignment of the array of test probes relative to the circuit array on the board; a driver for moving the board mounting plate and the test probes for thereby moving the circuit board relative to the fixed sensor to correct any misalignment of the circuit array relative to the array of test probes, the sensor producing the output to indicate the precise movement of the board mounting plate to an adjusted position relative to the probe plate necessary to align the sensor with the fiducial mark to thereby indicate precise alignment of the test probes with corresponding test points in the circuit array on the board.

But both U.S. Pat. Nos. 5,399,975 and 5,408,189 fail to solve the conventional disadvantages of the above problems (1) to (5)

SUMMARY OF THE INVENTION

Therefore, a first object of the present invention is to provide a method capable of easily and quickly testing an automatic inserting state of an electronic component in a PCB using a slit light.

A second object of the present invention is to provide an apparatus capable of easily and quickly testing an automatic inserting state of an electronic component in a PCB using a slit light.

In order to achieve the above first object, the present invention provides a method for testing an automatic insertion state of electronic components in a printed circuit board, the method comprising the steps of:

a) storing automatic insertion state data with respect to the electronic components in the printed circuit board;

b) moving a light source into a first testing area of the printed circuit board and irradiating a first testing light beam generated beam from the light source to the first testing area of the printed circuit board;

c) receiving a light reflected from the first testing area according to the irradiated light beam in the step b) and converting the received light into a pulse signal for judging an automatic insertion state having high and low levels;

d) analyzing characteristics of the converted pulse signal for judging an automatic insertion state in the step c), e) comparing the analyzing characteristics of the converted pulse signal for judging an automatic insertion state with the stored automatic insertion state data in the step a), and judging an automatic insertion state with respect to one of the electronic components corresponding to the first testing area according to a result of the comparison;

f) moving the light source into a second testing area of the printed circuit board and judging whether or not an automatic insertion state test for all testing areas of the printed circuit board is completed; and g) irradiating a second testing light beam to the second testing area, repeating the steps c), d), and e) when the automatic insertion state test for all testing areas of the printed circuit board is not completed in the step e), and completing all routine when the automatic insertion state test for all testing areas of the printed circuit board is not completed in the step e). Preferably, the automatic insertion state includes a normal state, a non-insertion state, an incorrect insertion, and a short state.

In order to achieve the above second object, the present invention provides an apparatus for testing an automatic insertion state of electronic components in a printed circuit board, the apparatus comprising:

a first means for storing automatic insertion state data with respect to the electronic components inserted in the printed circuit board;

a second means for irradiating a testing light beam to a testing area of the printed circuit board, receiving a light signal reflected according to the irradiated light beam from the testing area, and converting the received light signal into a pulse signal for judging an automatic insertion state;

a third means for moving the second means into a predetermined testing area of the printed circuit board; and a fourth means for controlling operations of the first means, the second means, and the third means, and comparing the pulse signal for judging an automatic insertion state from the second means with the stored automatic insertion state data in the first means, to judge the automatic insertion state of electronic components in the printed circuit board according to a result of the comparison.

Preferably, the automatic insertion state data with respect to the electronic components stored in the first means includes normal state data, non-insertion state data, incorrect insertion data, and short state data. Preferably, the second means includes a light source for irradiating a testing light beam to the first testing area of the printed circuit board, and a light receiving element for receiving a light reflected according to the irradiated light beam from the first area and converting the received light signal into a pulse signal for judging an automatic insertion state. More preferably, the automatic insertion state data of the electronic components includes a normal state, a non-insertion state, an incorrect insertion, and a short state.

As mentioned previously, the present invention makes use of a slit light type instead of using the conventional testing jig in order to test an automatic insertion state of an electronic component in a printed circuit board. Thus, the present invention can solve the problem of a noise generated when applying a signal and the signal indicates that the contacting pins of the electronic component contacting with pins of a jig are testing incorrect. Also, the present invention can reduce the setup time of an apparatus for testing an automatic insertion state of an electronic component in a printed circuit board according to changing a design of a PCB.

BRIEF DESCRIPTION OF THE DRAWINGS

The above objects and advantages of the present invention will become more apparent by describing in detail a preferred embodiment thereof with reference to the attached drawings, in which:

FIG. 9 is a flow chart for showing a method for testing an automatic insertion state of an electronic component in a printed circuit board according to one embodiment of the present invention.

DESCRIPTION OF THE PREFERRED EMBODIMENT

A description will be given below in detail, with reference to the accompanying drawings, of the mechanical structure, the circuitry configuration, and the operation of a method and an apparatus for testing an automatic inserting state of an electronic component in a printed circuit board according to one embodiment of the present invention.

Figure 1:
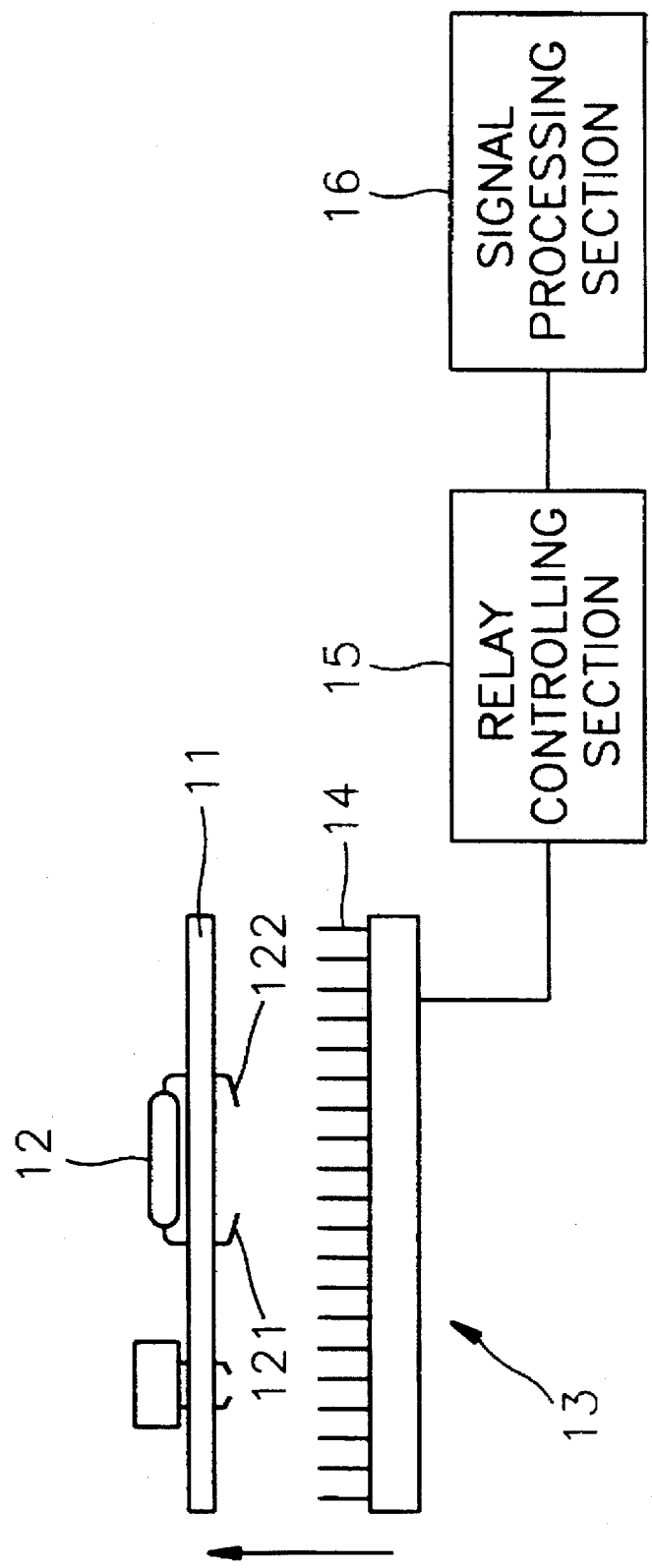
FIG. 1 is a block diagram for showing a configuration of a conventional apparatus for testing an automatic inserting state of an electronic component in a printed circuit board.
Figure 2:
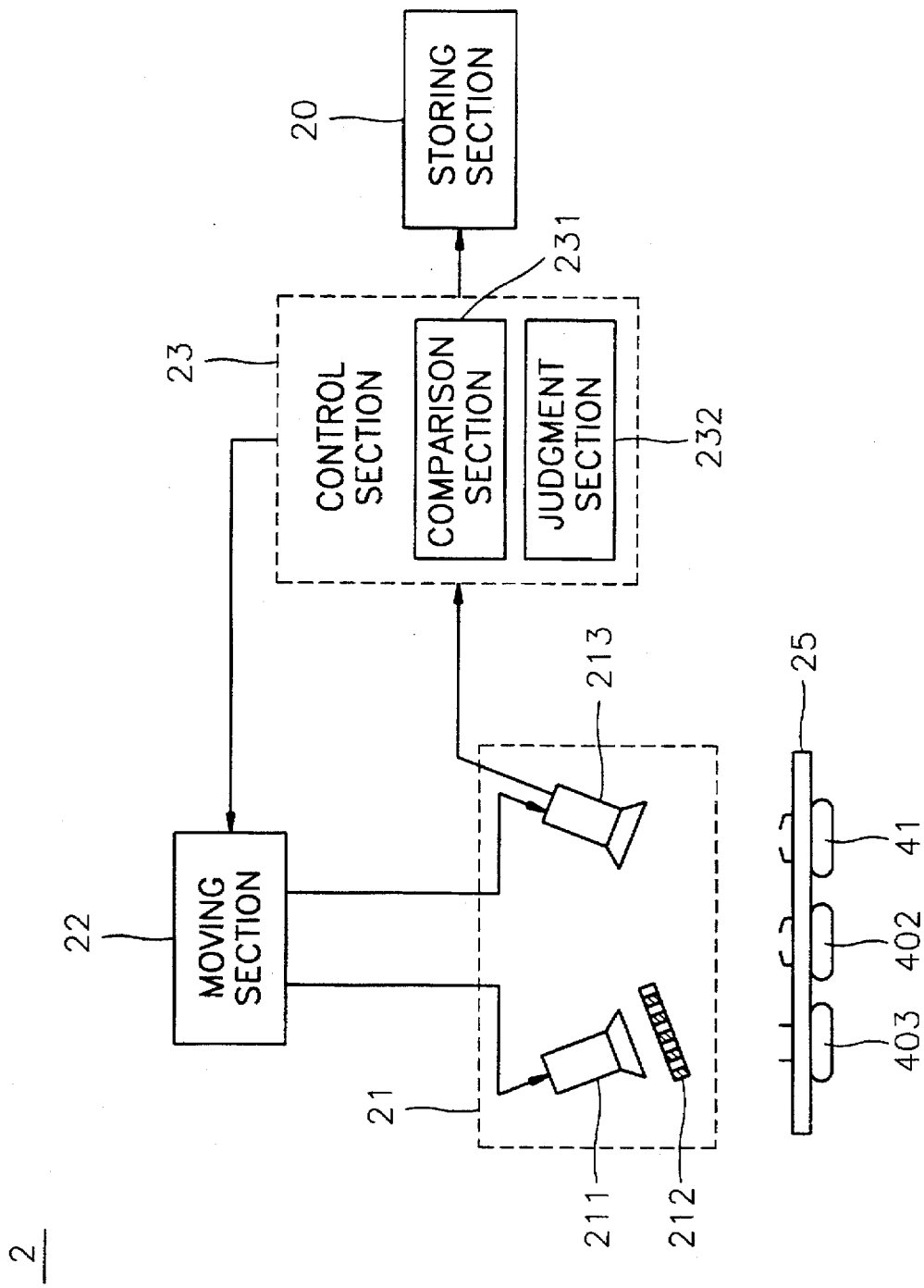
FIG. 2 is a block diagram for showing a configuration of an apparatus for testing an automatic insertion state of an electronic component in a printed circuit board according to one embodiment of the present invention.

FIG. 2 shows a configuration of an apparatus for testing an automatic insertion state of an electronic component in a printed circuit board according to one embodiment of the present invention.

The apparatus 2 includes a storing section 20 for storing automatic insertion state data with respect to the electronic components in a printed circuit board 25; a light detection section 21 for irradiating a testing light beam to a first testing area of the printed circuit board, receiving a light signal reflected according to the irradiated light beam from the first area, and converting the received light signal into a pulse signal; a moving section 22 for moving the light detection section into a testing area; and a control section 23 for controlling operations of storing section 20, light detection section 21, and moving section 22, comparing the pulse signal from light detection section 21 with the stored automatic insertion state data in order to judge the automatic insertion state of electronic components in printed circuit board 25.

Light detection section 21 includes a light source 211 for irradiating a testing light beam to the first testing area of printed circuit board 25, and a light receiving element 213 for receiving a light signal reflected according to the irradiated light beam from the first area and converting the received light signal into a pulse signal. Light detection section 21 further includes a slit 213 for convening the irradiated testing light beam to the first testing area of printed circuit board 25 from light source 211 in a slit light.

Figure 3A:
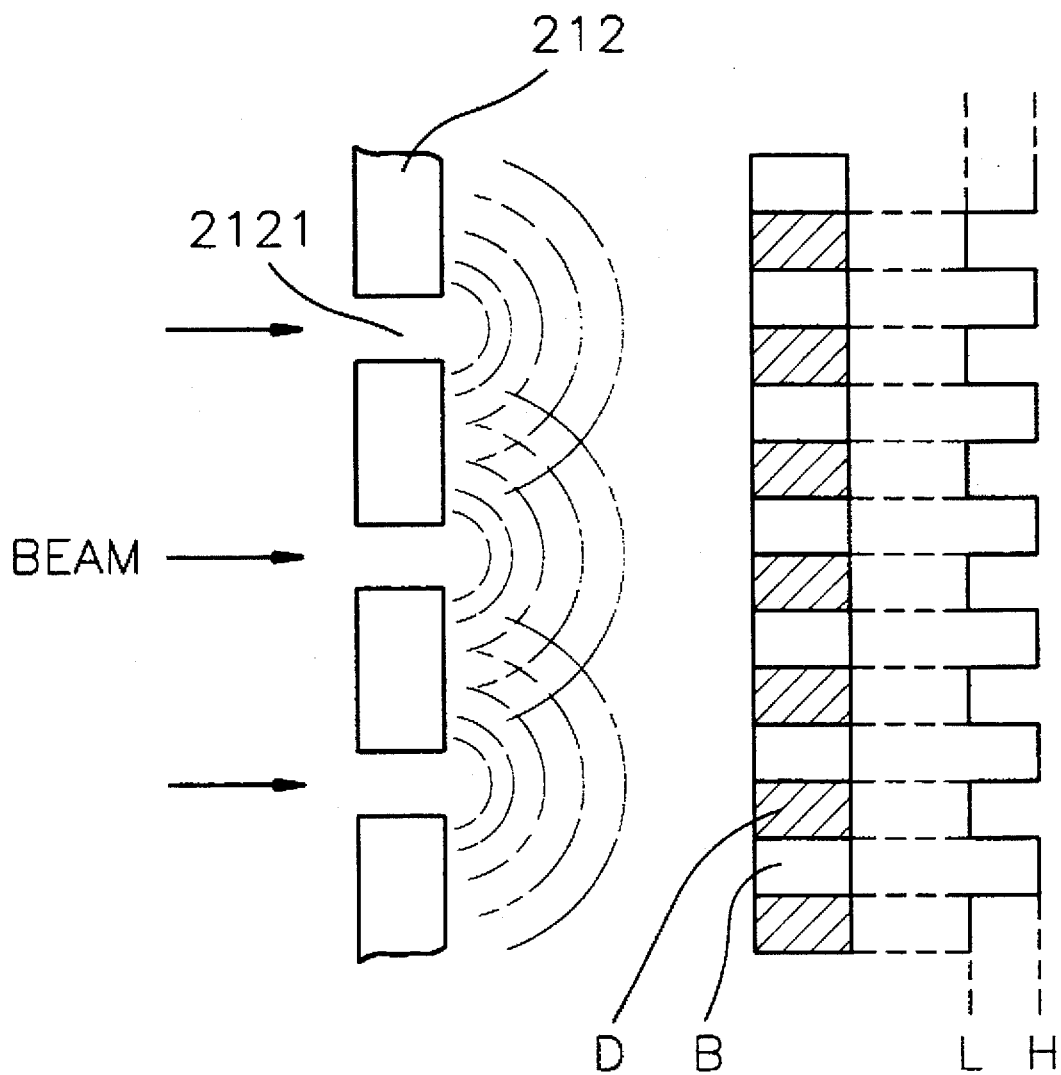
FIGS. 3A, 3B, to 3C are views for illustrating a principle of an apparatus and a method for testing an automatic inserting state of an electronic component in a printed circuit board.
Figure 3B:
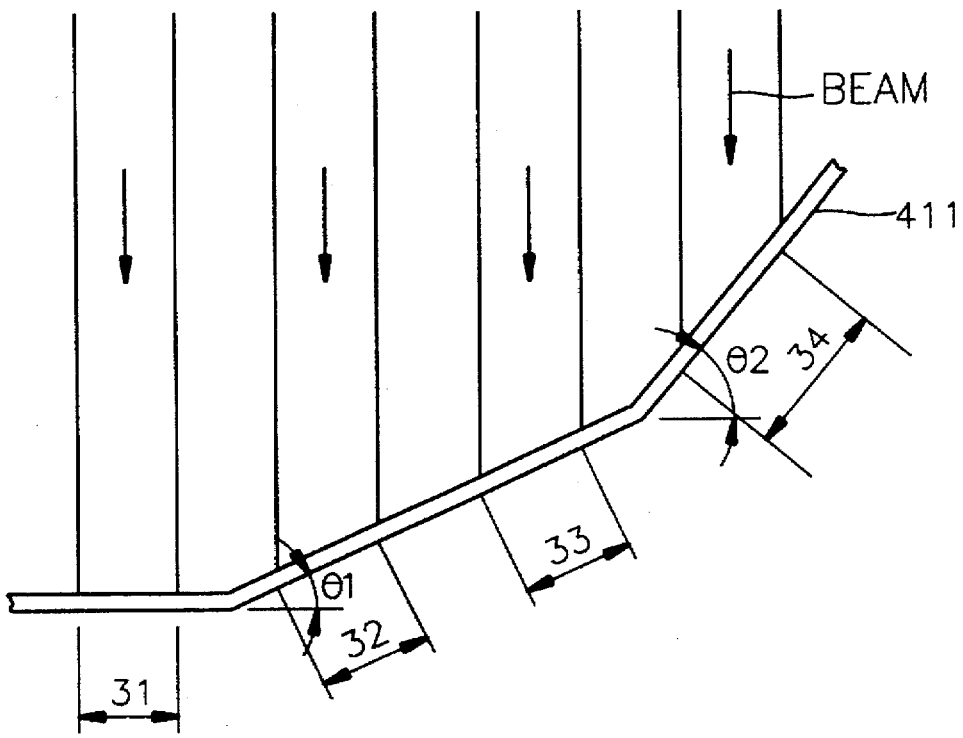
Figure 3C:

FIGS. 3A to 3C illustrates a principle of an apparatus and method for testing an automatic inserting state of an electronic component in a printed circuit board. When a light source (FIG. 2) irradiates a straight beam toward one direction of a slit 21 having a plurality of holes 22, a diffraction of a light is generated round holes 22 of slit 21 in the other direction. The diffraction of the light leads to superposition and interference according to a physical phenomenon in dark and bright places of slit 212, light receiving element 213 detects a light signal of the bright and dark places which is generated in a side of slit 212 according to the superposition and interference and converts the detected light signal into a pulse signal having high voltage (5 volts) and low voltage (0 volt) of pulse signal. The present invention is based upon a principle that a slit light is converted to a pulse signal when passed through slit 212.

As shown in FIG. 3C, pulse widths for a face 31 of pin 411 perpendicular to the irradiated light beam, faces 32 and 33 of pin 411 slanting to the irradiated light beam with an angle θ1, and a face 34 of pin 411 slanting to the irradiated light beam with an angle θ2 which is greater than the angle θ1, according to the reflected light beam, are all different. The widths of light beams reflected through the faces 31, 32, 33, and 34 when light source 211 irradiates a light beam of a constant size to PCB 25 through slit 212 are widest to narrowest in an order of 31<32=33<34.

Figure 4A:
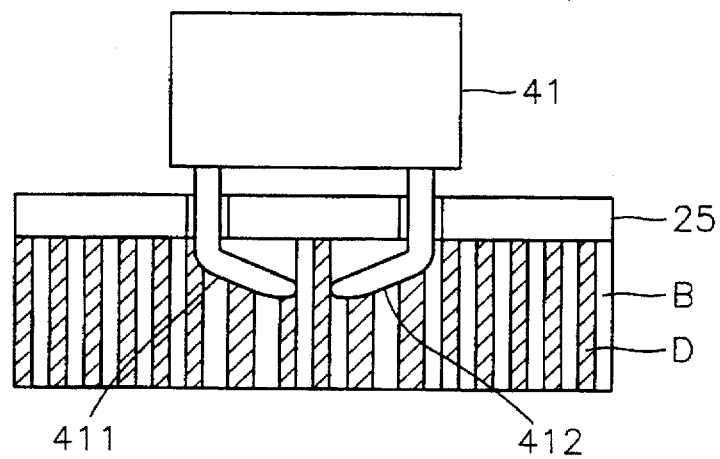
FIG. 4A is a view for showing a state which electronic component is correctly inserted into PCB.

FIG. 4A shows a state in which electronic component 41 is correctly inserted into PCB 25. Blank spaces B are parts in which the reflected beam is present, while deviant crease spaces D are parts in which the reflected beam is not present. A slope of first pin 411 of electronic component 41 is equal to that of second pin 42 thereof. There exists a regular interval between first pin 411 and second pin 412 thereof.

Figure 4B:
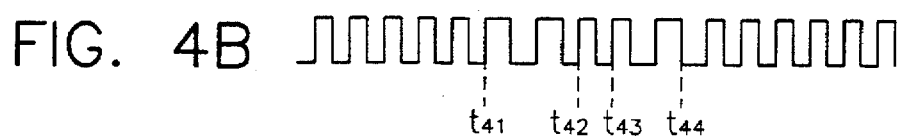
FIG. 4B is a view for showing a pulse signal according to a beam reflected in a light receiving element from PCB in the state of FIG. 4A.

FIG. 4B shows a pulse signal according to a beam reflected in a light receiving element 213 from PCB 25 in the state of FIG. 4A. Considering the width of the pulse signal reflected from PCB 25, the pulse width in slanting areas in which first and second pins 411 and 412 are inserted is wider than a reference pulse width. The reference pulse width exists between first pin 411 and second pin 412 of electronic component 41. Referring to FIG. 2, when light source 211 irradiates a light beam to PCB 25 through slit 212, light receiving element 213 receives a light beam reflected from PCB 25. Therefore, a width of the pulse signal in a part which first and second pins 411 and 412 of electronic component 41 are slanted at times $t_{41}$ to $t_{42}$ and $t_{43}$ to $t_{44}$ is wider than the reference width. A width of the pulse signal in the part between first pin 411 and second pin 412 of electronic component 41 at a time $t_{42}$ to $t_{43}$ is equal to the reference width.

Figure 4C:
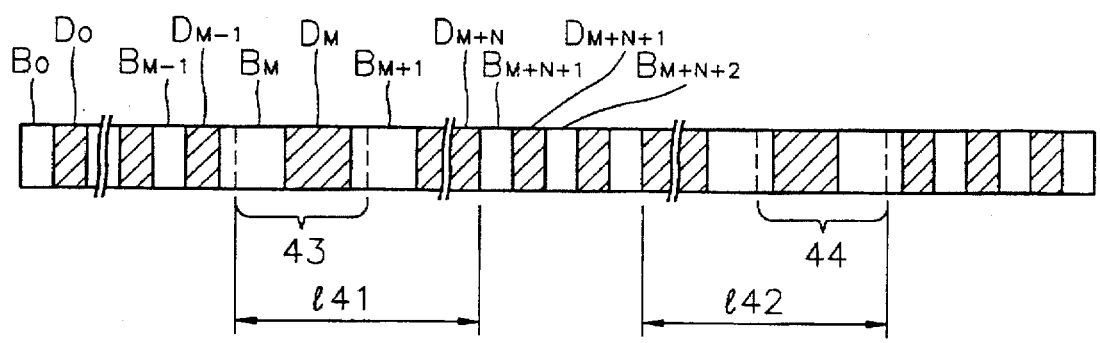
FIG. 4C is a view for illustrating a light receiving condition for judging a state of FIG. 4A.

FIG. 4C illustrates a light receiving condition for judging a state of FIG. 4A. Reference numerals 41 and 42 indicate holes reflected from PCB 25. $B_M$ is a bright part and $D_M$ is a dark part of hole 41. $l_{41}$ and $l_{42}$ are a slant part of first pin 411 and second pin 412 of electronic component 41, respectively. Control section 23 judges a state that a detection condition is $B_M > B_{M-1}$ and $D_M < D_{M-1}$, and that satisfies the following equation $B_M = B_{M+1} = B_{M+2} = \ldots = B_{M+N} > B_{M+N+1} = B_{M+N+2}$ as a normal state of FIG. 4A.

Figure 5A:
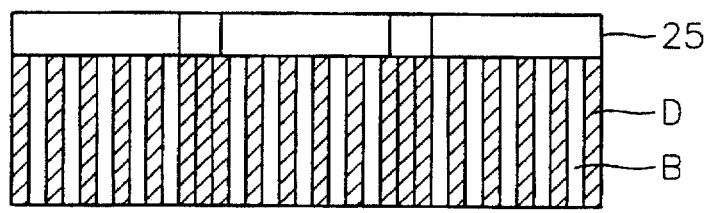
FIG. 5A is for showing a state which an electronic component is not inserted into PCB.

FIG. 5A shows a state which electronic component 41 is not inserted into PCB 25.

Figure 5B:
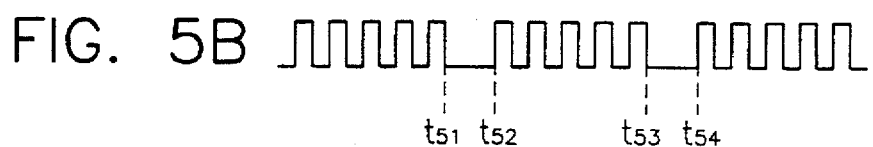
FIG. 5B is a view for showing a pulse signal according to a beam reflected in a light receiving section from a PCB in the state of FIG. 5A.

FIG. 5B shows a pulse signal according to a beam reflected in a light receiving element 213 from PCB 25 in the state of FIG. 5A. A width of high level "H" of the pulse signal reflected from PCB 25 is equal to that of a low level "L" of the pulse signal. That is, a user can know that holes of slit 212 are arranged at regular intervals. When light source 211 irradiates a light beam to PCB 25 through slit 212, light receiving element 213 receives no light beam reflected from PCB 25. Also, light receiving element 213 converts the no reflected light beam into a pulse signal having a low level "L". Therefore, the pulse signal having a low level "L" for times $t_{51}$ to $t_{52}$ and $t_{53}$ to $t_{54}$ is wider than the reference pulse width.

Figure 5C:
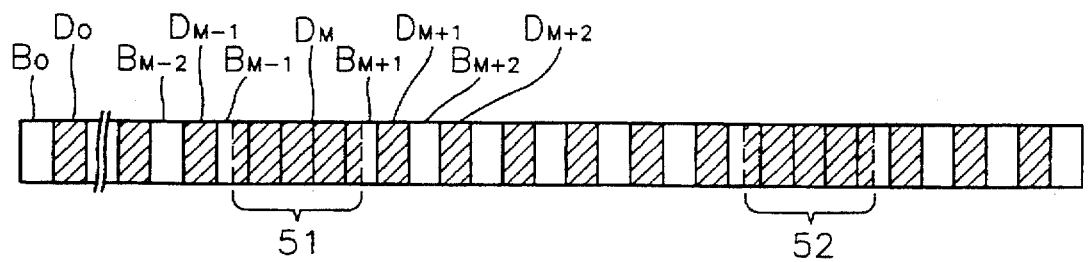
FIG. 5C is a view for illustrating a light receiving condition for judging a state of FIG. 5A.

FIG. 5C illustrates a light receiving condition for judging a state of FIG. 5A. Reference numerals 51 and 52 indicate holes reflected from PCB 25. Assumed that bright parts in front of the hole 41 are $B_{M-1}, B_{M-2}, B_{M-3}, \ldots B_2, B_1, B_0$, bright parts behind the hole 41 are $B_{M+1}, B_{M+2}, B_{M+3} \ldots$, dark parts in front of the hole 41 are $D_{M-1}, D_{M-2}, D_{M-3} \ldots D_2, D_1, D_0$, and dark parts behind the hole 41 are $D_{M+1}$, $D_{M+2}, D_{M+3} \ldots$, as much as a width of the slit light (or the reflected light). Control section 23 judges a state that a detection condition in which $B_0=B_1=B_2= \ldots =B_{M-1}$, $D_0=D_1=D_2=\ldots D_{M-1}=D_{M-1}$, and that satisfies the following equation $B_{M-2} \geq B_{M+1}, B_{M+2} \geq B_{M+1}, D_M > D_{M-2}, D_{M>DM+1}$ as the non-insertion of FIG. 5A.

Figure 6A:
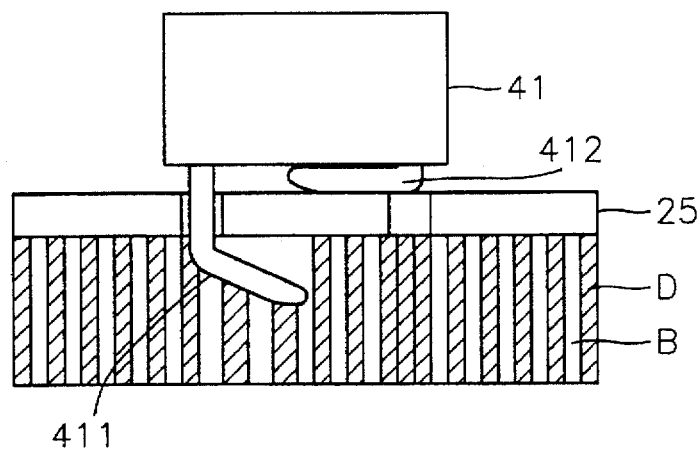
FIG. 6A is a view for showing a state which electronic component is incorrectly inserted into PCB.

FIG. 6A shows a state which electronic component 41 is incorrectly inserted into PCB 25. A first pin 411 of electronic component 41 is correctly inserted into a first hole 251 of PCB 25, while a second pin 412 of electronic component 41 is incorrectly inserted into a second hole 252 of PCB 25.

Figure 6B:
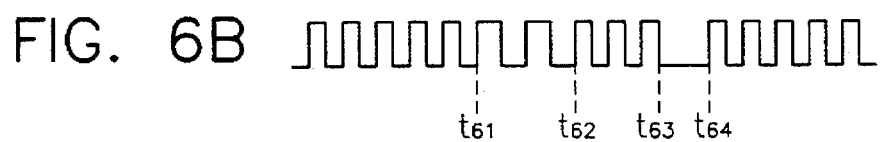
FIG. 6B is a view for showing a pulse signal according to a beam reflected in a light receiving section from a PCB in the state of FIG. 6A.

FIG. 6B shows a pulse signal according to a beam reflected in a light receiving element 213 from a PCB 25 in the state of FIG. 6A. A width of the pulse signal reflected from PCB 25 at a part in which first pin 411 of electronic component 41 is correctly inserted first 251 of PCB 25 is wider than that of other areas because first pin 411 of electronic component 41 is slanted. When light source 211 irradiates a light beam to PCB 25 through slit 212, light receiving element 213 receives a light beam reflected PCB 25PCB 25. Also, light receiving element 213 converts the reflected light beam into a pulse signal. Therefore, in the width of a pulse signal according to the reflected light beam, a width of the pulse signal from a second hole 252 of PCB 25 when pin 42 is not inserted into second hole 251 of PCB 25 is wider than the reference width of other areas. The second hole 252 of PCB 25 has a low level "L" of a pulse signal. A width of the pulse signal at an area when first pin 411 of electronic component 41 is slanted at times t61 to $t_{62}$ is wider than the width of the pulse signal from a second hole 252 of PCB 25 when pin 42 is not inserted into second hole 251 of PCB 25.

Figure 6C:
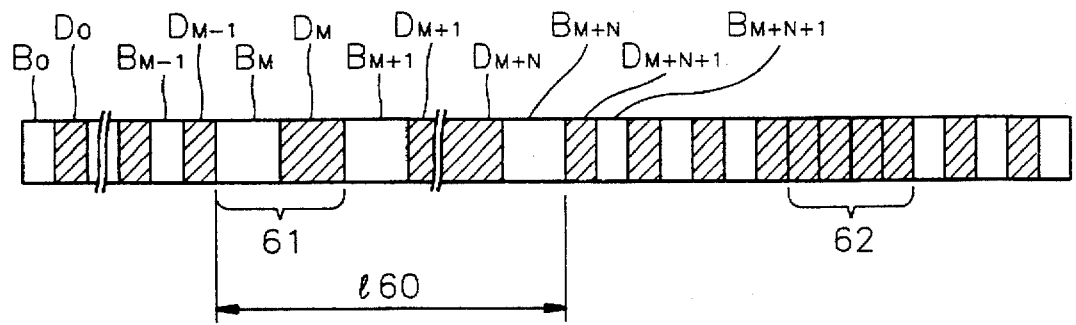
FIG. 6C is a view for illustrating a light receiving condition for judging a state of FIG. 6A.

FIG. 6C illustrates a light receiving condition for judging a state of FIG. 6A. Reference numerals 61 and 62 indicates holes reflected from PCB. A $l_{60}$ is a slanted part of first pin 411 of electronic component 41. Control section 23 judges a state which a detection condition is $B_0=B_1=B_2=\ldots =B_{M-1}$, $D_0=D_1=D_2= \ldots D_{M-2}=D_{M-1}$, and an area in which first pin 411 of electronic component 41 is correctly inserted into first hole 251 of PCB 25 satisfies the following equations $B_{M-1}<B_M= \ldots =B_{M+N}, B_{M+N}>B_{M+N+1}$, and $D_{M+N+N}>D_{M+N+1}$, and that an area in which second pin 412 of electronic component 41 is incorrectly inserted into second 252 of PCB 25 satisfies equations $B_{M-2} \geq B_{M-1}, B_{M+2} \geq B_{M+1}, D_M > D_{M-2} D_M > D_{M+1}$ in the state which the second pin 412 of electronic component 41 is inserted into second pin 251 of PCB 25 as the incorrect insertion of FIG. 6A.

Figure 7A:
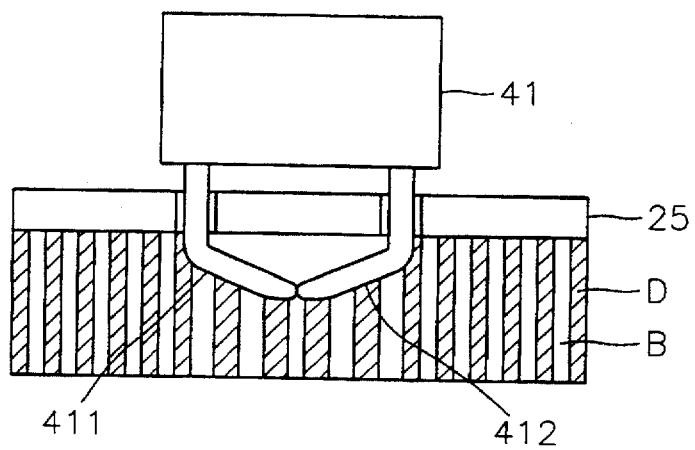
FIG. 7A is a view for showing a state which an electronic component is correctly inserted into PCB but one pin of the electronic component contacts with the other pin of electronic component so that the electronic component is in a short state.

FIG. 7A shows a state which electronic component 41 is correctly inserted into PCB 25 but first pin 411 of electronic component 41 contacts with the second pin 412 of electronic component 41 so that electronic component 41 is in a short state.

Figure 7B:
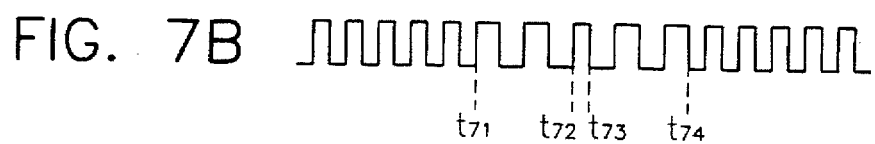
FIG. 7B is a view for showing a pulse signal according to a beam reflected in a light receiving element from a PCB in the state of FIG. 7A.

FIG. 7B shows a pulse signal according to a beam reflected in a light receiving element 213 from in the state of FIG. 7A. In the widths of pulse signals from any reflected light beam, a pulse width of slant parts generated by inserting first and second pins 411 and 412 of electronic component 41 into first and second holes 251 and 252 of PCB 25 is a little wider than other areas because of the slope of first and second pins 251 and 252 of electronic component 25. A pulse width of an area where first pin 411 of electronic component 41 contacts with second pin 412 thereof is narrower than that of other areas because pins 411 and 412 of electronic component 41 do not have a slope. When light source 211 irradiates a light beam to PCB 25 through slit 212, light receiving element 213 receives a light beam reflected from PCB 25. Also, light receiving element 213 converts the reflected light beam into a pulse signal. Therefore, in the width of the pulse signal from the pulse signal, the pulse widths of parts where first pin of electronic component 41 is slanted at times $t_{71}$ to $t_{72}$ and $t_{73}$ to $t_{74}$ are wider than a reference width of other areas. A pulse width of a part where first pin 411 of electronic component 41 contacts with second pin 412 thereof at time $t_{72}$ to $t_{73}$ is narrower than the reference width of other areas.

Figure 7C:
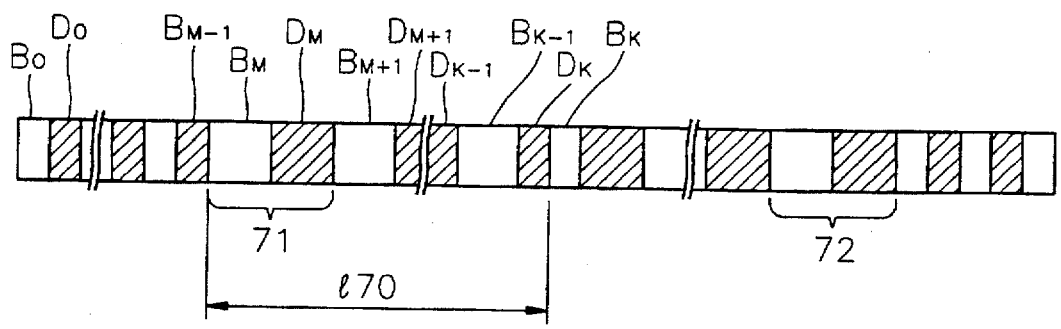
FIG. 7C is a view for illustrating a light receiving condition for judging a state of FIG. 7A.

FIG. 7C illustrates a light receiving condition for judging a state of FIG. 7A. Reference numerals 81 and 82 indicate holes reflected from PCB, respectively. A $l_{70}$ is slanted parts of first and second pins of electronic component. $B_K$ and $L_K$ are a bright part and a dark part in an area where first pin of electronic component contacts with second pin thereof. Control section 23 judges a state which a detection condition is that $B_M=B_{M+1}= \ldots =B_{K-1}=B_{K+1}$, and satisfies the following equations $B_K<B_{K-1}$ and $B_K<B_{K+1}$ as the short state of FIG. 7A. The K of $B_{K-1}, B_{K+1}$, and $B_K$ is M+2, M+3, M+4 ....

Figure 8A:
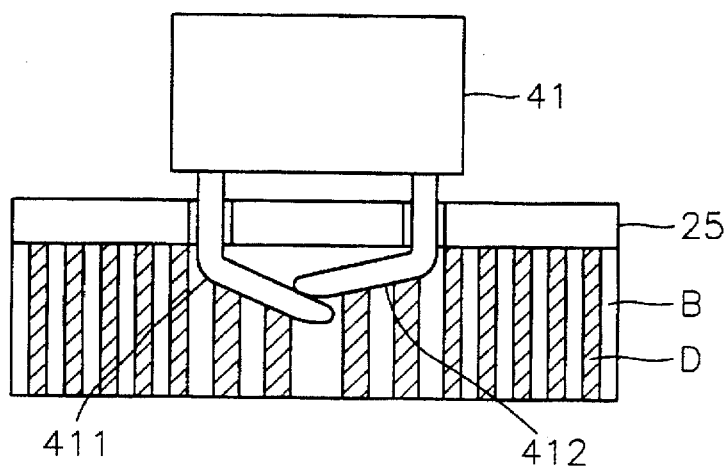
FIG. 8A is a view for showing a state which an electronic component is correctly inserted into PCB but one pin of the electronic component lies upon other pin thereof contacted each other so that the electronic component is in a short state.

FIG. 8A shows a state which electronic component 41 is correctly inserted into PCB 25 but second pin 412 of electronic component 41 lies upon first pin 411 thereof contacting each other so that electronic component 41 is in a short state.

Figure 8B:
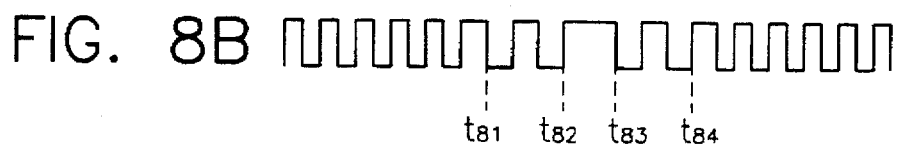
FIG. 8B shows a pulse signal according to a beam reflected in a light receiving element from a PCB in the state of FIG. 8A.

FIG. 8B shows a pulse signal according to a beam reflected in a light receiving element 213 from PCB 25 in the state of FIG. 8A. In the width of the pulse signal according to any reflected light beam, a pulse width of slant areas generated by inserting first and second pins 411 and 412 of electronic component 41 into first and second holes 251 and 252 of PCB 25 is wider than the reference width of other areas because of the slope of first and second pins 411 and 412 of electronic component 41. A pulse width at an area which second pin 412 of electronic component 41 lies upon first pin 412 thereof contacting each other is wider than that of the slanted areas because the first and second pins 411 and 412 deviate from a normal position thereof. When light source 211 irradiates a light beam to PCB 25 through slit 212, light receiving element 213 receives any light beam reflected from PCB 25. Also, light receiving element 213 converts the reflected light beam into a pulse signal. Therefore, in a width of the pulse signal from the pulse signal, a pulse width at areas where first and second pins 411 and 412 of electronic component 41 are slanted at times $t_{81}$ to $t_{82}$ and $t_{83}$ to $t_{84}$ are wider than a reference width of other areas. A pulse width at an area where second pin 412 of electronic component 41 lies on first pin 411 thereof at a time $t_{82}$ to $t_{83}$ is wider than that of the slanted area.

Figure 8C:
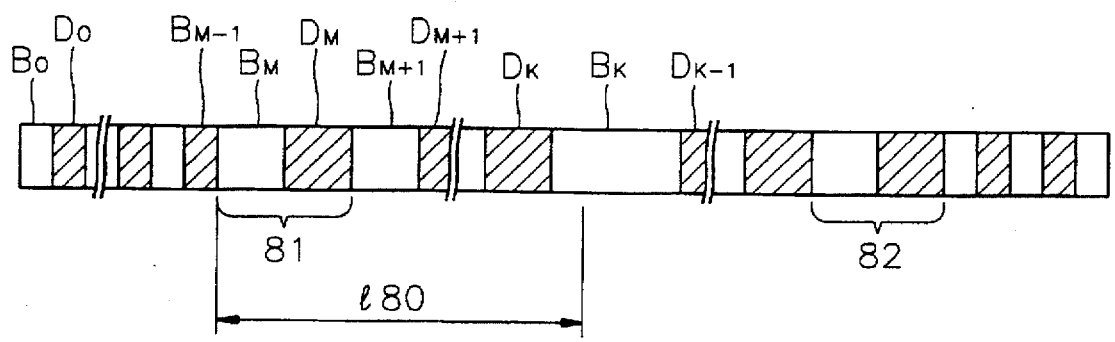
FIG. 8C is a view for illustrating a light receiving condition for judging a state of FIG. 8A.

FIG. 8C illustrates a light receiving condition for judging a state of FIG. 8A. Reference numerals 81 and 82 indicate holes reflected from PCB 25, respectively. A $l_{80}$ is a slanted part of first pin 411 of electronic component 41. A $B_K$ is a bright part which second pin 412 of electronic component 41 lies on first pin 411 thereof. Control section 23 judges a state which a detection condition is that $B_M=B_{M+1}=\ldots=B_{K-1}=B_{K+1}$, and satisfies the following equation $B_K>B_{K-1}$ as the short state of FIG. 7A. The K of $B_{K-1}$, $B_{K+1}$, $B_{K+2}$, $B_K$, and $B_{K-1}$ is M+2, M+3, M+4 . . . .

The operation of an apparatus 2 and a method for testing an automatic inserting state of an electronic component in a printed circuit board are described as follows. FIG. 9 is a flow chart for illustrating a method for testing an automatic insertion state of an electronic component in a printed circuit board according to one embodiment of the present invention.

At first, control section 23 controls storing section 20 to store the automatic insertion state data of electronic component 41 in PCB 25 therein (step S1). That is, storing section 20 stores data that a detection condition is $B_M>B_{M-1}$ and $D_M>D_{M-1}$, and that satisfies the following equations $B_M=B_{M+1}=B_{M+2}=\ldots=B_{M+N}>B_{M+N+1}=B_{M+N+2}$, as shown in FIGS. 4A to 4C as a normal state. Storing section 20 stores data that a detection condition is $B_0=B_1=B_2=\ldots=B_{M-1}$, $D_0=D_1=D_2=\ldots D_{M-1}=D_{M-1}$, and that satisfies the following equations $B_{M-2}\geq B_{M+1}$, $B_{M+2}\geq B_{M+1}$, $D_M>D_{M-2}$, $D_{M>DM+1}$, as shown in FIGS. 5A to 5C as a non-insertion state.

Storing section 20 stores data that a detection condition is $B_0=B_1=B_2=\ldots=B_{M-1}$, $D_0=D_1=D_2=\ldots D_{M-2}=D_{M-1}$, and that satisfies a following equations $B_{M-1}<B_M=\ldots=B_{M+N}$, $B_{M+N}>B_{M+N+1}$, and $D_{M+N}>D_{M+N+1}$, and $B_{M-2}\geq B_{M-1}$, $B_{M+2}\geq B_{M+1}$, $D_M>D_{M-2}$, $D_M>D_{M+1}$ as shown in FIGS. 6A to 6C as an incorrect insertion state. Storing section 20 stores data that a detection condition is $B_M=B_{M+1}=\ldots=B_{M+K-1}=B_{K+1}=B_{K+2}$, and that satisfies the following equation $B_K<B_{K-1}$ and $B_K<B_{K+1}$ as shown in FIGS. 7A to 7C as a state which electronic component 41 is correctly inserted into PCB 25 but first pin 411 of electronic component 41 contacts with the second pin 412 of electronic component 41 so that electronic component 41 is in a short state. Storing section 20 stores data that a detection condition is $B_M=B_{M+1}=\ldots=B_{M+K-1}=B_{K+1}=B_{K+2}$, and that satisfies the following equation $B_K<B_{K-1}$ as shown in FIGS. 8A to 8C as a state which electronic component 41 is correctly inserted into PCB 25 but second pin 412 of electronic component 41 lies upon first pin 411 thereof contacted each other so that electronic component 41 is in a short state.

When PCB 25 is mounted on an X-Y table (not shown), control section 23 controls moving section 22 to move PCB 25 into a first testing area (step S2).

Then, control section 23 applies a first controlling signal and a second signal controlling signal to light source 211 and light receiving element 213 of light detection section 21 to be operated. Accordingly, light source 211 irradiates a light beam to PCB 25 through slit 212 of light detection section 21 (step S3). Light receiving element 213 receives a light according to the irradiated light beam reflected from PCB 25 (step S4). Light receiving element 213 converts the light signal from PCB 25 into a pulse signal having a high level "H" or a low level "L"(step S5) and provides the pulse signal for control section 23.

At this time, control section 23 analyzes characteristics of the pulse signal from light receiving element 213 and comparing the analyzed characteristics of the pulse signal with the automatic insertion state data stored in storing section 20 in step S1 Control section 23 judges an automatic insertion state with respect to one of electronic components 41 corresponding to the first testing area according to the comparison (step S6). For instance, control section 23 judges a state as a normal state when a detection condition is $B_M>B_{M-1}$ and $D_M>D_{M-1}$, and satisfies the following equation $B_M=B_{M+1}=B_{M+2}=\ldots=B_{M+N}>B_{M+N+1}=B_{M+N+2}$, as shown in FIGS. 4A to 4C. Control section 23 judges the automatic insertion state as the non-insertion state when a detection condition is which $B_0=B_1B_2=\ldots=B_{M-1}$, $D_0=D_1=D_2=\ldots D_{M-1}=D_{M-1}$, and satisfies a following equations $B_{M-2}\geq B_{M-1}$, $B_{M+2}\geq B_{M+1}$, $D_M>D_{M-2}$, $D_M>D_{M+1}$, as shown in FIGS. 5A to 5C. Control section 23 judges a state as an incorrect insertion state when a detection condition is $B_0=B_1=B_2=\ldots=B_{M-1}$, $D_0=D_1=D_2=\ldots D_{M-2}=D_{M-1}$, and satisfies a following equations $B_{M-1}<B_M=\ldots=B_{M+N}$, $B_{M+N}>B_{M+N+1}$, and $D_{M+N}>D_{M+N+1}$, and $B_{M-2}\geq B_{M-1}$, $B_{M+2}\geq B_{M+1}$, $D_M>D_{M-2}$, $D_M>D_{M+1}$ as shown in FIGS. 6A to 6C. Control section 23 judges the automatic insertion state as a first short state when a detection condition is that $B_M=B_{M+1}=\ldots=B_{M+K-1}=B_{K+1}=B_{K+2}$, and satisfies the following equation $B_K>B_{M+K-1}$, as shown in FIGS. 7A to 7C. Control section 23 also judges the automatic insertion state as a second short state when a detection condition is $B_M=B_{M+1}=\ldots=B_{M+K-1}=\ldots=B_{M+K-1}=B_{K+1}=B_{K+2}$, and satisfies the following equations $B_{M+K-1}>B_{M+K}$ and $D_{M+K-1}>B_{M+K}$ as shown in FIGS. 8A to 8C.

After a test with respect to the automatic insertion state for the first area is completed, control section 23 controls moving section 22 to move light detection section 21 into a second testing area (step S8), and judges whether or not an automatic insertion state test for all testing areas is completed (step S9).

Then, in step S9, when it is judged that the automatic insertion state test for all testing areas is not completed, the routine returns to step S3 and performs the steps S3 to S8.

On the other, in step S9, when it is judged that the automatic insertion state test for all testing areas is completed, control section 23 draws off PCB 25 from an X-Y table (step S10). Then the routine finishes.

As mentioned previously, the present invention makes use of a slit light type instead of using the conventional testing jig in order to test an automatic insertion state of an electronic component in a printed circuit board. Thus, the present invention can solve the problem of a noise generated when applying a signal and the signal indicates that the contacting pins of the electronic component contacting with pins of a jig are testing incorrect. Also, the present invention can reduce the setup time of an apparatus for testing an automatic insertion state of an electronic component in a printed circuit board according to changing a design of a PCB. Further, since the present invention does not need a testing pin, it is low in price in an integrated PCB, Moreover, the present invention can extend the life of the electronic component and a PCB and simplify a configuration of the system because it does not require changing the testing pin.

The invention has been described in detail in connection with the preferred embodiment. This embodiment, however, is merely for example only and the invention is not restricted thereto. It will be easily understood by those skilled in the art that other variations and modifications can easily be made within the scope of this invention as defined by the appended claims.

What is claimed is:

1. A method for testing an automatic insertion state of electronic components in a printed circuit board, said method comprising the steps of:

a) storing automatic insertion state data with respect to the electronic components in the printed circuit board;

b) moving a light source into a first testing area of the printed circuit board and irradiating a first testing light beam generated beam from the light source to the first testing area of the printed circuit board;

c) receiving a light reflected from the first testing area according to the irradiated light beam in said step b) and converting the received light into a pulse signal for judging an automatic insertion state having high and low levels;

d) analyzing characteristics of the converted pulse signal for judging an automatic insertion state in said step c);

e) comparing the analyzing characteristics of the converted pulse signal for judging an automatic insertion state with the stored automatic insertion state data in said step a), and judging an automatic insertion state with respect to one of the electronic components corresponding to the first testing area according to a result of the comparison;

f) moving the light source into a second testing area of the printed circuit board and judging whether or not an automatic insertion state test for all testing areas of the printed circuit board is completed; and g) irradiating a second testing light beam to the second testing area, repeating said steps c), d), e) and f) when the automatic insertion state test for all testing areas of the printed circuit board is not completed in said step e), and completing all routine when the automatic insertion state test for all testing areas of the printed circuit board is not completed in said step f).

2. The method for testing an automatic insertion state of electronic components in a printed circuit board as claimed in claim 1, wherein the automatic insertion state includes a normal state, a non-insertion state, an incorrect insertion, and a short state.

3. The method for testing an automatic insertion state of an electronic component in a printed circuit board as claimed in claim 2, wherein the automatic insertion state is the normal state, when a pulse width in slanted areas where a first pin and a second pin of one electronic component of the electronic components corresponding to a testing area of the printed circuit board are inserted is wider than a reference width of the pulse signal for judging the automatic insertion state existing between the first pin and the second pin.

4. The method for testing an automatic insertion state of an electronic components in a printed circuit board as claimed in claim 2, wherein the automatic insertion state is the non-insertion state, when a width of the pulse signal having a high level or a low level is wider than the reference width of the pulse signal for judging the automatic insertion state.

5. The method for testing an automatic insertion state of an electronic components in a printed circuit board as claimed in claim 2, wherein the automatic insertion state is the incorrect insertion state, when a first width of the pulse signal for judging the automatic insertion state in an area where a first pin of one electronic component of the electronic components corresponding to a testing area of the printed circuit board is not inserted into the printed circuit board is wider than a reference width of the pulse signal for judging the automatic insertion state, and a second width of the pulse signal for judging the automatic insertion state at an area where a second pin of the one electronic component is slanted is wider than the first width.

6. The method for testing an automatic insertion state of an electronic components in a printed circuit board as claimed in claim 2, wherein the automatic insertion state is the short state, when pulse widths of first and second pins of one electronic component of the electronic components corresponding to a testing area of the printed circuit board are inserted into the printed circuit board and slanted are wider than a reference width of the pulse signal for judging the automatic insertion state, and a pulse width of an area where a first pin of electronic component contacts with a second pin thereof is narrower than the reference width of the pulse signal for judging the automatic insertion state.

7. The method for testing an automatic insertion state of an electronic components in a printed circuit board as claimed in claim 2, wherein the automatic insertion state is the short state, when first widths of the pulse signal at areas where first and second pins of one electronic component of the electronic components corresponding to a testing area of the printed circuit board are inserted into the printed circuit board and slanted are wider than a reference width of the pulse signal for judging the automatic insertion state, and a second width at an area where the first pin of the electronic component lies on the second pin thereof is wider than the first widths.

8. A method for testing an automatic insertion state of electronic components in a printed circuit board, said method comprising the steps of:

i) storing automatic insertion state data with respect to the electronic components in the printed circuit board;

ii) moving a light source into a first testing area of the printed circuit board and irradiating a first testing light beam generated beam from the light source to the first testing area of the printed circuit board;

iii) receiving a light reflected from the first testing area according to the irradiated light beam in said step b);

iv) converting the received light in said iii) into a pulse signal for judging an automatic insertion state having high and low levels;

v) analyzing characteristics of the converted pulse signal for judging an automatic insertion state in said step iv);

vi) comparing the analyzing characteristics of the converted pulse signal for judging an automatic insertion state with the stored automatic insertion state data in said step i);

vii) judging an automatic insertion state with respect to one of the electronic components corresponding to the first testing area according to a result of the comparison in said vi);

viii) moving the light source into a second testing area of the printed circuit board and judging whether or not an automatic insertion state test for all testing areas of the printed circuit board is completed; and ix) irradiating a second testing light beam to the second testing area, repeating said steps iii) to viii) when the automatic insertion state test for all testing areas of the printed circuit board is not completed in said step viii), and completing all routine when the automatic insertion state test for all testing areas of the printed circuit board is not completed in said step viii).

9. An apparatus for testing an automatic insertion state of electronic components in a printed circuit board, the automatic insertion state including a normal state, a non-insertion state, an incorrect insertion, and a short state, said apparatus comprising:

a first means for storing automatic insertion state data with respect to the electronic components inserted in the printed circuit board, the automatic insertion state data with respect to the electronic components stored in said first means includes normal state data, non-insertion state data, incorrect insertion data, and short state data;

a second means for irradiating a testing light beam to a testing area of the printed circuit board, receiving a light signal reflected according to the irradiated light beam from the testing area, and converting the received light signal into a pulse signal for judging an automatic insertion state having high and low levels, said second means including a light source for irradiating a testing light beam to the first testing area of the printed circuit board, and a light receiving element for receiving a light reflected according to the irradiated light beam from the first area and converting the received light signal into the pulse signal for judging the automatic insertion state:

a third means for moving said second means into a predetermined testing area of the printed circuit board; and a fourth means for controlling operations of said first means, said second means, and said third means, for analyzing characteristics of the converted pulse signal for judging the automatic insertion state and for comparing the pulse signal for judging an automatic insertion state from said second means with the stored automatic insertion state data in said first means, to judge the automatic insertion state of electronic components in the printed circuit board according to a result of the comparison, wherein said fourth means includes a comparison section for comparing the pulse signal for judging the automatic insertion state from said second means with the automatic insertion state data stored in said first means, and a judgement section for judging the automatic insertion state of electronic components according to the result of the comparison by means of said comparison section.

10. The apparatus for testing an automatic insertion state of electronic components in a printed circuit board as claimed in claim 9, wherein said second means further includes a slit for converting the irradiated testing light beam to the first testing area of the printed circuit board from said light source in a slit light.

11. The apparatus for testing an automatic insertion state of electronic components in a printed circuit board as claimed in claim 9, wherein the automatic insertion state is in the normal state, when pulse widths in slanted areas where a first pin and a second pin of one electronic component of the electronic components corresponding to testing area of the printed circuit board are inserted, are wider than a reference width of the pulse signal for judging the automatic insertion state, according to the result of the comparison by means of said fourth means.

12. The apparatus for testing an automatic insertion state of an electronic components in a printed circuit board as claimed in claim 9, wherein the automatic insertion state is the non-insertion state, when a width of the pulse signal having a high level or a low level is wider than the reference width of the pulse signal for judging the automatic insertion state, according the result of the comparison by means of said fourth means.

13. The apparatus for testing an automatic insertion state of an electronic components in a printed circuit board as claimed in claim 9, wherein the automatic insertion state is the incorrect insertion state, when a first width of the pulse signal for judging the automatic insertion state in an area where a first pin of one electronic component of the electronic components corresponding to a testing area of the printed circuit board is not inserted into the printed circuit board is wider than a reference width of the pulse signal for judging the automatic insertion state, and a second width of the pulse signal for judging the automatic insertion state at an area where a second pin of the one electronic component is slanted is wider than the first width, according the result of the comparison by means of said fourth means.

14. The apparatus for testing an automatic insertion state of electronic components in a printed circuit board as claimed in claim 9, wherein the automatic insertion state is the short state, when pulse widths of the pulse signal at areas where first and second pins of one electronic component of the electronic components corresponding to a testing area of the printed circuit board are inserted into the printed circuit board and slanted, are wider than a reference width of the pulse signal for judging the automatic insertion state, and a pulse width of an area where the first pin of electronic component contacts with the second pin is narrower than the reference width of the pulse signal for judging the automatic insertion state, according to the result of the comparison by means of said fourth means.

15. The apparatus for testing an automatic insertion state of an electronic components in a printed circuit board as claimed in claim 9, wherein the automatic insertion state is the short state, when first widths of the pulse signal at areas where first and second pins of one electronic component of the electronic components corresponding to a testing area of the printed circuit board are inserted into the printed circuit board and slanted are wider than a reference width of the pulse signal for judging the automatic insertion state, and a second width at an area where the first pin of the electronic component lies on the second pin thereof is wider than the first widths, according the result of the comparison by means of said fourth means.

* * * * *